United States Patent

Gates et al.

Patent Number: 5,559,081
Date of Patent: Sep. 24, 1996

[54] SULFONAMIDE HERBICIDES

[75] Inventors: Peter S. Gates; Graham P. Jones; David E. Saunders, all of Cambridge, England

[73] Assignee: Agrevo UK Limited, England

[21] Appl. No.: 232,297

[22] PCT Filed: Nov. 2, 1992

[86] PCT No.: PCT/EP92/02558

§ 371 Date: May 6, 1994

§ 102(e) Date: May 6, 1994

[87] PCT Pub. No.: WO93/09099

PCT Pub. Date: May 13, 1993

[30] Foreign Application Priority Data

Nov. 7, 1991 [GB] United Kingdom ........ 9123711
Mar. 25, 1992 [GB] United Kingdom ........ 9206458
Mar. 25, 1992 [GB] United Kingdom ........ 9206459
Mar. 25, 1992 [GB] United Kingdom ........ 9206460
Mar. 25, 1992 [GB] United Kingdom ........ 9206475
Jul. 7, 1992 [GB] United Kingdom ........ 9214400

[51] Int. Cl.$^6$ .......... C07D 239/32; C07D 403/12; C07D 403/14; A01N 43/54

[52] U.S. Cl. .......... 504/242; 544/296; 544/284; 544/254; 544/262; 544/300; 544/301; 544/310; 544/312; 544/316; 544/317; 544/319; 544/327; 544/333; 544/334; 544/335; 504/239; 504/240; 504/241; 504/243

[58] Field of Search ............ 504/242, 243, 504/239, 240, 241; 544/300, 301, 310, 312, 316, 317, 319, 296, 284, 254, 262

[56] References Cited

PUBLICATIONS

Furya et al, Chemical Abstracts, vol. 105, entry 42476 (1986).

*Primary Examiner*—John M. Ford
*Attorney, Agent, or Firm*—Ostrolenk, Faber, Gerb & Soffen, LLP

[57] ABSTRACT

Herbicidal sulfonamides of the formula:

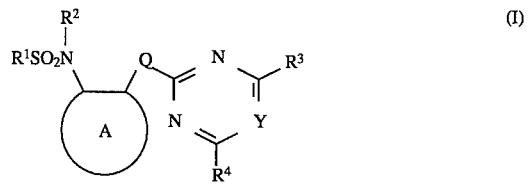

and salts thereof, where: A represents a substituted or unsubstituted benzene ring, or a 5- or 6-membered substituted or unsubstituted heteroaromatic ring; Q is —O—, —S— or a group —CXX'—; X and X', which may be the same or different, are each hydrogen, halogen, cyano, an optionally-substituted alkyl group, or a group —$OR^a$, —$SR^a$, or —$COR^b$; or one of X and X' represents hydroxy and the other is as defined above; or X and X' together represent =O or =S; $R^a$ is an optionally-substituted alkyl, aryl or acyl group; $R^b$ is an optionally-substituted alkyl or aryl group, or a group —$OR^c$ or —$NR^cR^d$; $R^c$ and $R^d$, which may be the same or different, are each hydrogen, or an optionally-substituted alkyl or aryl group; Y is nitrogen or a group $CR^9$; $R^1$ is an optionally-substituted alkyl, alkenyl, alkynyl, cycloalkyl, aryl, heterocyclyl, benzoheterocyclyl or amino group; $R^2$ is hydrogen, an optionally-substituted alkyl or carboxylic acyl group, or a group —$SO_2R^1$; $R^3$ and $R^4$, which may be the same or different, are each hydrogen, halo, an optionally substituted alkyl, alkoxy, cycloalkyl or amino group, or an optionally substituted heterocyclyl group; and $R^9$ represents hydrogen or an optionally-substituted alkyl group.

17 Claims, No Drawings

SULFONAMIDE HERBICIDES

This application is a 371 of PCT/EP92/02558, filed Nov. 2, 1992.

This invention concerns herbicidal sulfonamides, processes for their preparation, and compositions containing them.

EP 363040 and WO 91/10653 each disclose herbicidal sulfonanilides related to those of the present invention.

In one aspect, the invention provides novel sulfonamides of the formula:

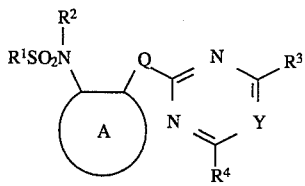

(I)

and salts thereof, where:

A represents a substituted or unsubstituted benzene ring, or a 5-membered substituted or unsubstituted heteroaromatic ring;

Q is —O—, —S— or a group —CXX'—;

X and X', which may be the same or different, are each hydrogen, halogen, cyano, an optionally-substituted alkyl group, or a group —OR$^a$, —SR$^a$, or —COR$^b$; or one of X and X' represents hydroxy and the other is as defined above; or X and X' together represent =O or =S;

R$^a$ is an optionally-substituted alkyl, aryl or acyl group;

R$^b$ is an optionally-substituted alkyl or aryl group, or a group —OR$^c$ or —NR$^c$R$^d$;

R$^c$ and R$^d$, which may be the same or different, are each hydrogen, or an optionally-substituted alkyl or aryl group;

Y is nitrogen or a group CR$^9$;

R$^1$ is an optionally-substituted alkyl, alkenyl, alkynyl, cycloalkyl, aryl, heterocyclyl, benzoheterocyclyl or amino group;

R$^2$ is hydrogen, an optionally-substituted alkyl or carboxylic acyl group, or a group —SO$_2$R$^1$;

R$^3$ and R$^4$, which may be the same or different, are each hydrogen, halo, an optionally-substituted alkyl, alkoxy, cycloalkyl or amino group, or an optionally-substituted heterocyclyl group; and R$^9$ represents hydrogen or an optionally-substituted alkyl group;

with the proviso that, when Q is —O— or —S—, the ring A is a 5-membered substituted or unsubstituted heteroaromatic ring;

and with the proviso that, when R$^1$ is substituted alkyl, it is not a group of the formula:

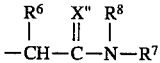

where X" is oxygen or sulfur, and R$^6$, R$^7$ and R$^8$ are each hydrogen or optionally-substituted alkyl.

When A is a 5-membered heteroaromatic ring, it is preferably a substituted or unsubstituted thiophene, furan, pyrrole, thiazole, isothiazole, pyrazole, imidazole, oxazole or isoxazole ring.

In the ring A, any substituent on a carbon atom thereof is preferably halo, cyano, a group —COOR$^{10}$ (where R$^{10}$ represents hydrogen or an optionally-substituted alkyl group), or an optionally-substituted alkyl, alkoxy, aryloxy, heterocyclyloxy or amino group. Preferred such substituent groups are fluoro and chloro.

Any substituent on a nitrogen atom of the ring A is preferably a substituted or unsubstituted alkyl, alkoxy, amino or aryl group, especially a methyl group.

Any alkyl group present in the molecule is preferably of 1 to 8 carbon atoms, especially of 1 to 6 carbon atoms, and particularly of 1 to 4 carbon atoms. Specific preferred unsubstituted alkyl or alkyl-containing groups include methyl, ethyl, n-propyl, isopropyl, n-butyl, t-butyl, methoxy, ethoxy and n-propoxy.

When any alkyl group in the molecule is substituted, this may for example be by one or more halogen atoms (eg fluorine, chlorine or bromine), alkoxy or alkylthio groups of 1 to 4 carbon atoms (eg methoxy or ethoxy), hydroxy, nitro, mercapto, amino, substituted amino, carbamoyl, substituted carbamoyl, thiocarbamoyl, substituted thiocarbamoyl, cyano, acyl, aryl or heteroaryl groups. Specific preferred substituted alkyl-containing groups include chloromethyl, bromomethyl, dichloromethyl, trifluoromethyl, difluoromethoxy, cyanomethyl, methoxyethyl and ethoxyethyl.

Any alkenyl or alkynyl group in the molecule is preferably of 2 to 6 carbon atoms, for example vinyl, allyl or propargyl. Any such alkenyl or alkynyl group is preferably unsubstituted, though it may if desired be substituted for example by halogen.

Any cycloalkyl group in the molecule is preferably of 3 to 7, especially of 5 or 6 carbon atoms, especially a cyclopentyl or cyclohexyl group. It is preferably unsubstituted.

Any aryl group in the molecule is preferably a phenyl group, which is desirably substituted by one or more alkyl, alkoxy, alkoxycarbonyl or alkylthio groups of 1 to 4 carbon atoms (which may themselves be further substituted), halogen atoms, cyano groups, aminosulfonyl groups or nitro groups, especially a phenyl group substituted by one or more chlorine, bromine or fluorine atoms, and/or one or more methyl, methoxy, trifluoromethyl, methylthio, methoxycarbonyl, ethoxycarbonyl or nitro groups.

Any heterocyclyl group in the molecule, other than the ring A, is preferably furyl, thienyl, or a nitrogen-containing heterocycle, for example a 5- or 6-membered single ring heterocycle, eg pyrrolyl, oxazolyl, isoxazolyl, isothiazolyl, pyrimidinyl, triazolyl or imidazolyl. R$^1$ may also with advantage represent pyridyl, furyl, thienyl, or a bicyclic heterocyclyl group, eg a thiazolotriazolyl, triazolopyrimidinyl or pyrazolopyrimidinyl group.

Any benzoheterocyclyl group in the molecule is preferably a benzothiophene, benzodioxole, quinoline, quinazoline, benzothiazole or dihydrobenzofuran group.

Any halogen atom present in the molecule is preferably fluorine, chlorine or bromine.

Any substituted amino group in the molecule may be mono- or di-substituted, for example by alkyl of 1 to 4 carbon atoms, alkenyl of 2 to 4 carbon atoms, carbamoyl, or carboxylic acyl, alkoxycarbonyl, alkylcarbamoyl or dialkylcarbamoyl in which any alkyl group is of 1 to 4 carbon atoms.

The term 'acyl' is used herein to mean the residue of carboxylic, sulfonic or phosphorus-containing acids, for example alkanoyl, alkenoyl, alkynoyl, cycloalkanoyl, aralkanoyl, aroyl, carbamoyl, thiocarbamoyl, alkoxycarbonyl, sulfonyl, sulfamoyl and phosphonyl groups, in which any alkyl, alkenyl, alkynyl or aryl group may be substituted or unsubstituted.

Specific preferred groups which R$^1$ may represent include methyl, chloromethyl, bromomethyl, cyanomethyl, trifluoromethyl and 2,2,2-trifluoroethyl.

R$^2$ preferably represents hydrogen.

R$^3$ and R$^4$ are each desirably hydrogen, methyl, methoxy or chloro. It is particularly preferred for R$^3$ and R$^4$ to be identical, and especially for both to be methoxy.

The ring A is preferably benzene (optionally substituted by fluorine, chlorine, bromine, methyl, methoxy or ethoxy), or pyrazole (optionally substituted by one or more methyl groups).

Q is preferably —CH$_2$—, —CH(CH$_3$)—, —S— or —O—.

The salts of the compounds of formula I are preferably those formed with strong bases such as alkali-metal (eg potassium or sodium) salts and amine salts (eg triethylamine, di-isopropylamine, cyclohexylamine or piperidine salts).

Particularly preferred compounds according to the invention are those of the Examples provided hereinafter.

In another aspect, the invention provides a process for the preparation of a sulfonamide of formula I in which a corresponding amine of the formula:

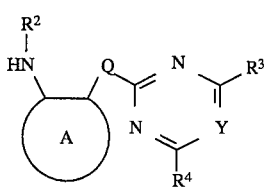
(II)

where A, Q, Y, and R$^2$ to R$^4$ are as defined hereinbefore is reacted with a suitable sulfonic anhydride of the formula (R$^1$SO$_2$)$_2$O or sulfonyl halide of the formula R$^1$SO$_2$Hal, where Hal is a halogen atom and R$^1$ is as defined hereinbefore, to give the desired compound.

The reaction is desirably effected in the presence of a base, for example an organic base such as pyridine.

The compounds of formula II may themselves be prepared by a process in which a substituted amine of the formula:

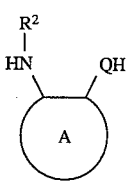
(III)

where A, Q and R$^2$ are as defined hereinbefore, is reacted in the presence of a base with a compound of the formula:

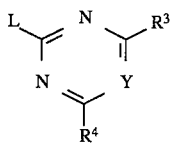
(IV)

where Y, R$^3$ and R$^4$ are as defined hereinbefore, and L is a leaving group, to give the desired compound.

The leaving group L may be any suitable such group, but is preferably a halogen atom, especially a chlorine atom, or a methylsulfonyl group.

The base employed is preferably an alkyllithium, eg t-butyllithium, and the reaction is desirably effected in a suitable solvent medium, eg tetrahydrofuran.

The compounds of formula II where R$^2$ is hydrogen may alternatively be prepared by reduction of the corresponding nitro compounds of the formula:

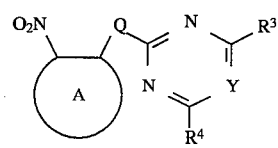
(V)

where A, Q, Y, R$^3$ and R$^4$ are as defined hereinbefore.

The reduction is conveniently effected by means of stannous chloride, or alternatively using iron in an acid medium, especially in trifluoroacetic acid and/or anhydride, by methods known per se. This latter procedure first produces a compound in which the nitro group is converted into a group —NHCOCF$_3$, which is then converted to an amino group by the action of a base, eg potassium carbonate.

Compounds of formula II may if desired be converted into other compounds of formula II by methods known per se. For example, the compounds of formula II where X or X' is an alkyl group may be prepared from the corresponding compounds of formula II where Q is —CH$_2$— and R$^2$ is hydrogen by first protecting the amino group, eg by reacting the compound with di-t-butyl dicarbonate, then subjecting the protected compound to the action of an alkylating agent, eg methyl iodide, in the presence of a strong base, and then removing the protection on the amino group, eg by means of trifluoroacetic acid.

The compounds of formula V may themselves be prepared by a process in which a compound of the formula:

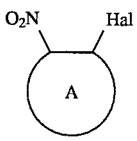
(VI)

where A is as defined hereinbefore and Hal represents a halogen atom, is reacted in the presence of a base with a compound corresponding to formula IV where R$^3$ and R$^4$ are as defined hereinbefore but L represents a group —QH where Q is as defined hereinbefore.

The compounds of formula V may alternatively be prepared by a process in which a nitro compound of the formula:

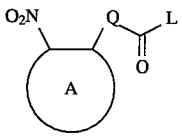
(VII)

where A, B, D and Q are as defined hereinbefore and L represents a leaving group (preferably chloro or imidazol-1-yl) is reacted in the presence of a base with a compound of the formula R$^3$C(=NH)YHC(=NH)R$^4$ where Y, R$^3$ and R$^4$ are as defined hereinbefore.

The base is preferably diisopropylethylamine.

The compounds of formula I where R$^1$ is a group of the formula:

be prepared by a process in which a corresponding compound of formula I in which R$^1$ represents a group of the formula CH$_3$OCOCHR$^6$— where R$^6$ is as defined hereinbefore is reacted with an amine of the formula R$^7$R$^8$NH where R$^7$ and R$^8$ are as defined hereinbefore to give the desired compound.

The reaction is desirably effected in a suitable solvent medium, for example an alcohol such as methanol.

The starting materials of formula I in the above process may be prepared, when $R^2$ is hydrogen, by a process in which a compound of formula II where $R^2$ is hydrogen is reacted in the presence of a base with a sulfonyl chloride of the formula:

$$ClO_2SCHR^6CO_2CH_3$$

where $R^6$ is as defined hereinbefore to give the desired compound.

The base employed is preferably a tertiary organic base, eg pyridine, and the reaction is desirably effected in a suitable solvent medium, eg dichloromethane.

The starting materials of formula I in the above process in which $R^2$ is other than hydrogen may be prepared from the corresponding compounds where $R^2$ is hydrogen by acylation techniques known per se.

The compounds of formula I in which $R^1$ is a group of the formula:

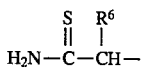

may be prepared by a process in which a cyanoalkyl compound of formula I where $R^1$ is a group of formula $NCCHR^{6-}$ is reacted in a suitable solvent medium with hydrogen sulfide to give the desired compound.

The compounds of formula II where A represents an N-methylpyrazole ring, and $R^2$ represents hydrogen, may alternatively be prepared by a process in which a dimethylaminoacrylonitrile of the formula:

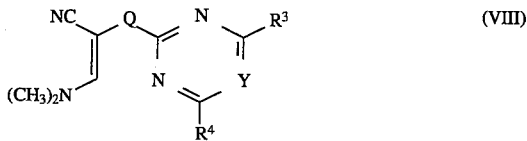

where Q, Y, $R^3$ and $R^4$ are as defined hereinbefore is reacted with methylhydrazine in acetic acid to give the desired compound.

The starting materials in the above processes, in particular the compounds of formulae III, IV, VI, VII and VIII, are either known compounds or may be prepared by processes analogous to those known for related similar compounds which are well known to those skilled in the art.

The salts of the compounds of formula I may be prepared by methods known per se from the corresponding free compounds by subjecting them to the action of a suitable base in a suitable solvent (eg an ether).

The compounds of formula I in which $R^2$ is other than hydrogen may alternatively be prepared from the salts of the compounds of formula I by reaction thereof in a manner known per se with a suitable alkylating or acylating agent containing the desired group $R^2$.

The compounds of formula I are herbicidally-active against a wide range of broad-leaved and grassy weeds, but are comparatively safe to certain crop species. They may thus be of use as selective herbicides, particularly in the control of a range of weeds in cereals, sugar beet or other crops, eg wheat, barley, maize, soya beans, oilseed rape, cotton or rice.

Accordingly, in another aspect, this invention provides a method of combating weeds at a locus infested or liable to be infested therewith, which comprises applying to said locus an effective amount of one or more compounds of formula I.

Desirable rates of application of the compounds of formula I or their salts range from 0.001 to 2 kg/ha, particularly from 0.005 to 1.0 kg/ha, and especially from 0.01 to 0.5 kg/ha.

In another aspect, the invention provides a composition which comprises one or more compounds of the invention in association with a suitable carrier and/or surface active agent.

The compositions usually contain from 0.01 to 99% by weight of the present compounds, and are normally produced initially as concentrates containing from 0.5 to 99%, preferably from 0.5 to 85%, and especially from 10 to 50% by weight thereof. Such concentrates are diluted if necessary before application to the locus to be treated such that the active ingredient comprises from 0.01 to 5% by weight of the formulation applied.

The carrier may be water, in which case an organic solvent may also be present, though this is not usually employed. A flowable suspension concentrate may be formed by grinding the compound with water, a wetting agent and a suspending agent, e.g. xanthan gum.

The carrier may alternatively be a water immiscible organic solvent, e.g. a hydrocarbon which boils within the range 130°–270° C., e.g. xylene, in which the compound is dissolved or suspended. An emulsifiable concentrate containing a water immiscible solvent may be formed with a surface active agent so that the concentrate acts as a self-emulsifiable oil on admixture with water.

The carrier may alternatively be a water-miscible organic solvent e.g. 2-methoxyethanol, methanol, propylene glycol, diethylene glycol, diethylene glycol monoethyl ether, methylformamide or dimethylformamide.

The carrier may alternatively be a solid, which may be finely divided or granular. Examples of suitable solids are limestone, clays, sand, mica, chalk, attapulgite, diatomite, perlite, sepiolite, silicas, silicates, lignosulfonates and solid fertilizers. The carrier can be of natural or synthetic origin or can be modified natural material.

Wettable powders soluble or dispersible in water may be formed by admixing the compound in particulate form with a particulate carrier or spraying molten compound on to the particulate carrier, admixing a wetting agent and a dispersing agent and finely grinding the whole powder mixture.

An aerosol composition may be formed by admixing the compound with a propellant, e.g. a polyhalogenated alkane such as dichlorofluoromethane, and suitably also with a solvent.

The term 'surface active agent' is used in the broad sense to include materials variously called emulsifying agents, dispersing agents and wetting agents. Such agents are well known in the art.

The surface active agents used may comprise anionic surface active agents, for example mono- or di-esters of phosphoric acid with a fatty alcohol ethoxylate, or salts of such esters, fatty alcohol sulfates such as sodium dodecyl sulfate, ethoxylated fatty alcohol sulfates, ethoxylated alkylphenol sulfates, lignin sulfates, petroleum sulfonates, alkylaryl sulfonates such as alkyl-benzene sulfonates or lower alkylnaphthalene sulfonates, salts of sulfonated naphthaleneformaldehyde condensates, salts of sulfonated phenolformaldehyde condensates, or more complex sulfonates such as the amide sulfonates, e.g. the sulfonated condensation product of oleic acid and N-methyl taurine or the dialkyl sulfosuccinates e.g. the sodium sulfonate of dioctyl succinate.

The surface active agents may also comprise non-ionic agents, for example condensation products or fatty acid esters, fatty alcohols, fatty acid amides or alkyl-substituted phenols with ethylene oxide, fatty esters of polyhydric alcohol ethers e.g. sorbitan fatty acid esters, condensation products of such esters with ethylene oxide e.g. polyoxyethylene sorbitan fatty acid esters, block copolymers of ethylene oxide and propylene oxide, acetylenic glycols such as 2,4,7,9-tetramethyl-5-decyne-4,7-diol, or ethoxylated acetylenic glycols.

The surface active agents may also comprise cationic agents, for example alkyl- and/or aryl-substituted quaternary ammonium compounds such as cetyl trimethylammonium bromide, or ethoxylated tertiary fatty amines.

Preferred surface active agents include ethoxylated fatty alcohol sulfates, lignin sulfonates, alkyl-aryl sulfonates, salts of sulfonated naphthaleneformaldehyde condensates, salts of sulfonated phenolformaldehyde condensates, sodium oleoyl N-methyltauride, dialkyl sulfosuccinates, alkyl phenol ethoxylates, and fatty alkyl ethoxylates.

The present active compounds, especially those of the Examples provided hereinafter, may be admixed with another pesticide, eg a herbicide, fungicide or insecticide, or a plant growth regulator, particularly another herbicide. Suitable further herbicides include trietazine, linuron, MCPA, dichlorprop, isoxaben, diflufenican, metolachlor, fluometuron, oxyfluorfen, fomesafen, bentazone, prometryne, norflurazon, chlomazone, EPTC, imazaquin, more especially isoproturon, methabenzthiazuron, trifluralin, ioxynil, bromoxynil, benazolin, mecoprop, fluroxypyr, alachlor, acifluorfen, lactofen, metribuzin and pendimethalin, and most particularly ethofumesate and phenmedipham.

The present compounds may be applied to plants, the soil, land or aquatic areas, and particularly to a locus at which a crop is growing or is about to grow. The compounds are active both pre- and post-emergence.

The invention is illustrated by the following Examples.

EXAMPLE A

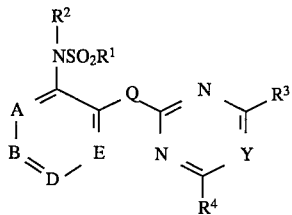

(Ia)

EXAMPLE A1

1,1,1-Trifluoro-2'-(4,6-dimethoxypyrimidin-2-ylmethyl) methanesulfonanilide (a) 2-(4,6-Dimethoxypyrimidin-2-ylmethyl)aniline Method 1 n-Butyl lithium (21 ml of 2.5M in hexane) was added dropwise to a stirred solution of o-toluidine (5.35 g) in dry tetrahydrofuran (100 ml) at −70° C. under nitrogen. The resulting suspension was allowed to warm to 5° C. to give a pale yellow solution. Dry carbon dioxide was bubbled int the mixture for about 6 minutes. The solvent was removed by stirring under high vacuum at room temperature to give a white solid. This was suspended in dry tetrahydrofuran and cooled to −70° C. under nitrogen. t-Butyl lithium (70 ml of 1.6M in pentane) was added dropwise over 15 minutes. The mixture was then allowed to warm to −15° C. and was stirred at this temperature for 75 minutes. The mixture was cooled to −70° C. and a solution of 4,6-dimethoxy-2-methylsulfonylpyrimidine (10.9 g) in tetrahydrofuran was added dropwise. The mixture was stirred at −75° C. for 60 minutes and then at room temperature overnight. The solvent was removed under vacuum, and 2N hydrochloric acid was added to the residue under nitrogen with ice-water cooling. A further 250 ml of water was added and the cloudy solution was basified with saturated sodium bicarbonate solution and extracted with ether (2×400 ml). The combined extracts were washed with saturated sodium chloride solution, dried and evaporated to give an orange oil, which was purified by chromatography to give 2 g of the product as a yellow solid, mp 82°–84° C.

Method 2

(i) 4,6-Dimethoxy-2-(2-nitrobenzyl)pyrimidine

Ethyl diisopropylamine (240 ml) was added dropwise to a stirred suspension of dimethyl malonimidate dihydrochloride (73.2 g) in dichloromethane (400 ml) at −40° C. under nitrogen, and the mixture was stirred at −40° C. for 25 minutes to give suspension A. 2-Nitrophenylacetic acid (65.16 g) was added portionwise to a stirred suspension of carbonyl diimidazole (53.3 g) in dichloromethane (400 ml) at room temperature. The resulting solution was stirred for 10 minutes and was added dropwise over 30 minutes to the suspension A at −40° C. The mixture was stirred at −40° C. for a further 45 minutes and then at room temperature overnight, after which the solution was washed with water (400 ml), 2N HCl (400 ml) and saturated sodium bicarbonate solution (400 ml), dried and evaporated to give an orange solid. It was then stirred with propan-2-ol (50 ml) for 10 minutes and filtered. The solid was washed with a further 50 ml of propan-2-ol and then dried to give 32.6 g of the desired product as a yellow solid, mp 92°–93° C.

(ii) 2-(4,6-Dimethoxypyrimidin-2-ylmethyl)aniline

The product of stage (i) (32.6 g) was added to a stirred suspension of stannous chloride dihydrate (133 g) in ethanol (300 ml). After refluxing for 2 hours, the solution was poured into ice-water (2500 ml) and extracted with ethyl acetate (3×500 ml). The combined extracts were washed with saturated sodium chloride solution, dried and evaporated to give 24.3 g of the desired product as a brown solid, mp 82°–84° C.

(b) 1,1,1-Trifluoro-2'-(4,6-dimethoxypyrimidin-2-ylmethyl) methanesulfonanilide

Trifluoromethanesulfonic anhydride (1.12 g) was added dropwise to a stirred solution of 2-(4,6-dimethoxypyrimidin-2-ylmethyl)aniline (0.98 g) plus pyridine (0.31 g) in dry dichloromethane (15 ml) at −70° C. under nitrogen. The resulting orange solution was stirred at −75° C. for 2 hours and then allowed to warm to room temperature and stirred for a further hour. The mixture was washed with water, dried and evaporated to give a red oil. Purification by chromatography and recrystallisation from 60/80 petroleum ether gave 0.4 g of the product as a white solid, mp 99°–100° C.

EXAMPLE A2

1,1,1-Trifluoro-2'-[1-(4,6,-dimethoxypyrimidin-2-yl)ethyl) methanesulfonanilide (a) t-Butyl [2-(4,6-dimethoxypyrimidin-2-ylmethyl)phenyl]carbamate A solution of the product of Example A1 stage (a) (24.1 g) and di-tert-butyl dicarbonate (24 g) was refluxed in dry tetrahydrofuran (250 ml) under nitrogen for 4 hours. The solvent was evaporated to give a brown oil, which was crystallised from hexane (200 ml) to give 28 g of the desired compound as a light brown solid, mp 98°–100° C.

(b) t-Butyl [2-[1-(4,6-dimethoxypyrimidin-2-yl)ethyl]phenyl]carbamate

The product of stage (a) above (1 g) was dissolved in dry tetrahydrofuran (20 ml) and tetramethyl ethylenediamine (1.1 ml) was added under nitrogen. The solution was cooled to −70° C. and 1.7M t-butyllithium in pentane (4.3 ml) was added dropwise. The mixture was then stirred at about −20° C. for 1 hour. It was then cooled to −70° C., and methyl iodide (0.45 g) was added. The reaction mixture was allowed to warm to 0° C. and saturated ammonium chloride solution (25 ml) was added. The mixture was extracted with tetrahydrofuran (3×50 ml) and the combined extracts were dried and evaporated to give a pale brown solid which was triturated with hexane to give 0.73 g of the desired product, mp 119°–121° C.

(c) 2-[1-(4,6-Dimethoxypyrimidin-2-yl)ethyl]aniline

The product of stage (b) above (5.0 g) was added to trifluoroacetic acid (25 ml) and the resulting solution was stirred at room temperature for 3 hours. The solution was evaporated and the residue was triturated with diisopropyl ether and cooled in a solid carbon dioxide-acetone bath. The solid was filtered and washed with diisopropyl ether to give 3.5 g of the desired product, mp 136°–139° C.

(d) 1,1,1-Trifluoro-2'-[1-(4,6-dimethoxypyrimidin-2-yl)ethyl]methanesulfonanilide Starting with the product of stage (c) above, the title compound was prepared by a method analogous to that of Example A1 stage (b), mp 132°–133° C.

EXAMPLE A3

1,1,1-Trifluoro-2'-(4,6-dimethoxy-1,3,5-triazin-2-ylmethyl)methanesulfonanilide

(a) 2,4-Dimethoxy-6-(2-nitrobenzyl)-1,3,5-triazine

Carbonyl diimidazole (3.34 g) was added portionwise to a stirred suspension of 2-nitrophenylacetic acid (3.4 g) in dichloromethane (30 ml), and the mixture was stirred at room temperature for 30 minutes. The resulting red solution was added dropwise to a stirred suspension of dimethyl imidodicarbonimidate zinc salt (3.0 g) in dichloromethane (25 ml) at −35° C. The reaction mixture was stirred at room temperature overnight and then poured onto water (100 ml). The mixture was extracted with dichloromethane (3×50 ml) and the combined extracts were dried and evaporated to give a red oil which was triturated with ether to give 1.41 g of the desired product as a pale brown solid, mp 91.6°–92.3° C.

(b) 1,1,1-Trifluoro-2'-(4,6-dimethoxy-1,3,5-triazin-2-ylmethyl)methanesulfonanilide Starting with the product of stage (a) above, the title compound was prepared by a method analogous to that of Example A1(a) Method 2(ii) and A1(b), mp 101°–108° C.

EXAMPLE A4

N-[3-(4,6-dimethoxypyrimidin-2-ylmethyl)-2-pyridyl]-1,1,1-trifluoromethanesulfonamide

(a) t-Butyl (3-methyl-2-pyridyl)carbamate

A solution of 2-amino-3-methylpyridine (20 g) plus di-t-butyl dicarbonate (46.8 ml) in dry tetrahydrofuran was refluxed for 3 hours. The solution was evaporated to give a dark brown oil. This was dissolved in ethyl acetate (400 ml), washed with 1.0N citric acid (3×200 ml) and saturated sodium chloride solution, dried, and evaporated to give a pale yellow solid which was crystallised from hexane/diisopropyl ether (1:2) to give 6.5 g of the desired compound as a pale yellow solid, mp 135°–137° C.

(b) t-Butyl [3-(4,6-dimethoxypyrimidin-2-ylmethyl)-2-pyridyl]carbamate n-Butyllithium (19.2 ml of a 2.5M solution in hexane) was added dropwise to a stirred suspension of the product of stage (a) above (5.0 g) in dry tetrahydrofuran (100 ml) under nitrogen at −70° C. The mixture was stirred at −70° C. for 20 minutes and then at 5° C. for 3 hours. It was then cooled to −70° C. and treated with 4,6-dimethoxy-2-methylsulfonylpyrimidine (5.42 g), and the mixture was stirred at −70° C. for 1 hour, then at room temperature overnight. Saturated ammonium chloride solution (500 ml) was added, and the mixture was extracted with ethyl acetate (2×100 ml). The combined extracts were washed with saturated sodium chloride solution (50 ml), dried and evaporated to give an orange oil which was triturated with hexane to give 5.35 g of the desired product as a pale yellow solid, mp 89°–92° C.

(c) N-[3-(4,6-dimethoxypyrimidin-2-ylmethyl]-2-pyridyl]-1,1,1-trifluoromethanesulfonamide Starting with the product of stage (b) above, the title compound was prepared by a method analogous to that of Example A1 stage (b), mp 124°–126° C.

EXAMPLES A5–A17

The following compounds of formula Ia where A is $=CR^5-$; Q is $-CH_2-$; $R^2$ is H; B, D and E are each $=CH-$; and $R^3$ and $R^4$ are each methoxy, may be prepared by methods analogous to that of Example A1 above:

| Ex | Y | $R^5$ | $R^1$ | M Pt (°C.) |
|---|---|---|---|---|
| A5 | CH | H | $CH_2CN$ | 116–117 |
| A6 | CH | Cl | $CH_2CN$ | 162–163 |
| A7 | CH | Cl | $CF_3$ | 113–115 |
| A8 | CH | F | $CH_2CN$ | 162–163 |
| A9 | CH | F | $CF_3$ | 100–102 |
| A10 | CH | Me | $CH_2CN$ | |
| A11 | CH | Me | $CF_3$ | |
| A12 | N | F | $CH_2CN$ | orange oil |
| A13 | N | F | $CF_3$ | |
| A14 | N | Me | $CH_2CN$ | |
| A15 | N | Me | $CF_3$ | |
| A16 | N | Cl | $CH_2CN$ | 31 |
| A17 | N | Cl | $CF_3$ | orange oil |

EXAMPLES A18–A20

The following compounds of formula Ia where A is nitrogen, Q is —CH$_2$—; R$^2$ is H; B, D and E are each =CH—; and R$^3$ and R$^4$ are each methoxy, may be prepared by methods analogous to that of Example A1 above:

| Ex | Y | R$^1$ | M Pt (°C.) |
|---|---|---|---|
| A18 | CH | CH$_2$CN | |
| A19 | N | CH$_2$CN | |
| A20 | N | CF$_3$ | |

EXAMPLES A21–A68

The following compounds of formula Ia where R$^2$ is hydrogen, R$^3$ and R$^4$ are both methoxy, and Q is —CH$_2$—, may be prepared by methods as described hereinbefore:

| Ex | Y | R$^1$ | A | B | D | E |
|---|---|---|---|---|---|---|
| A21 | CH | CF$_3$ | N | N | CH | CH |
| A22 | CH | CF$_3$ | N | CH | N | CH |
| A23 | CH | CF$_3$ | N | CH | CH | N |
| A24 | CH | CF$_3$ | CH | N | N | CH |
| A25 | CH | CF$_3$ | CH | N | CH | N |
| A26 | CH | CF$_3$ | CH | CH | N | N |
| A27 | CH | CF$_3$ | CCl | N | N | CH |
| A28 | CH | CF$_3$ | CCl | N | CH | N |
| A29 | CH | CF$_3$ | CCl | CH | N | N |
| A30 | CH | CF$_3$ | CF | N | N | CH |
| A31 | CH | CF$_3$ | CF | N | CH | N |
| A32 | CH | CF$_3$ | CF | CH | N | N |
| A33 | CH | CH$_2$CN | N | N | CH | CH |
| A34 | CH | CH$_2$CN | N | CH | N | CH |
| A35 | CH | CH$_2$CN | N | CH | CH | N |
| A36 | CH | CH$_2$CN | CH | N | N | CH |
| A37 | CH | CH$_2$CN | CH | N | CH | N |
| A38 | CH | CH$_2$CN | CH | CH | N | N |
| A39 | CH | CH$_2$CN | CCl | N | N | CH |
| A40 | CH | CH$_2$CN | CCl | N | CH | N |
| A41 | CH | CH$_2$CN | CCl | CH | N | N |
| A42 | CH | CH$_2$CN | CF | N | N | CH |
| A43 | CH | CH$_2$CN | CF | N | CH | N |
| A44 | CH | CH$_2$CN | CF | CH | N | N |
| A45 | N | CF$_3$ | N | N | CH | CH |
| A46 | N | CF$_3$ | N | CH | N | CH |
| A47 | N | CF$_3$ | N | CH | CH | N |
| A48 | N | CF$_3$ | CH | N | N | CH |
| A49 | N | CF$_3$ | CH | N | CH | N |
| A50 | N | CF$_3$ | CH | CH | N | N |
| A51 | N | CF$_3$ | CCl | N | N | CH |
| A52 | N | CF$_3$ | CCl | N | CH | N |
| A53 | N | CF$_3$ | CCl | CH | N | N |
| A54 | N | CF$_3$ | CF | N | N | CH |
| A55 | N | CF$_3$ | CF | N | CH | N |
| A56 | N | CF$_3$ | CF | CH | N | N |
| A57 | N | CH$_2$CN | N | N | CH | CH |
| A58 | N | CH$_2$CN | N | CH | N | CH |
| A59 | N | CH$_2$CN | N | CH | CH | N |
| A60 | N | CH$_2$CN | CH | N | N | CH |
| A61 | N | CH$_2$CN | CH | N | CH | N |
| A62 | N | CH$_2$CN | CH | CH | N | N |
| A63 | N | CH$_2$CN | CCl | N | N | CH |
| A64 | N | CH$_2$CN | CCl | N | CH | N |
| A65 | N | CH$_2$CN | CCl | CH | N | N |
| A66 | N | CH$_2$CN | CF | N | N | CH |
| A67 | N | CH$_2$CN | CF | N | CH | N |
| A68 | N | CH$_2$CN | CF | CH | N | N |

EXAMPLES A69–A126

The following compounds of formula Ia where R$^2$ is H, R$^3$ and R$^4$ are both methoxy, A is =CR$^5$—, and Q is —CH$_2$—, may be prepared by methods as described hereinbefore:

| Ex | Y | R$^1$ | R$^5$ | B | D | E | M Pt (°C.) |
|---|---|---|---|---|---|---|---|
| A69 | CH | CF$_3$ | H | N | CH | CH | |
| A70 | CH | CF$_3$ | H | CH | N | CH | |
| A71 | CH | CF$_3$ | H | CH | CH | N | |
| A72 | CH | CF$_3$ | Cl | N | CH | CH | |
| A73 | CH | CF$_3$ | Cl | CH | N | CH | |
| A74 | CH | CF$_3$ | Cl | CH | CH | N | |
| A75 | CH | CF$_3$ | F | N | CH | CH | |
| A76 | CH | CF$_3$ | F | CH | N | CH | |
| A77 | CH | CF$_3$ | F | CH | CH | N | |
| A78 | CH | CH$_2$CN | H | N | CH | CH | |
| A79 | CH | CH$_2$CN | H | CH | N | CH | |
| A80 | CH | CH$_2$CN | H | CH | CH | N | |
| A81 | CH | CH$_2$CN | Cl | N | CH | CH | |
| A82 | CH | CH$_2$CN | Cl | CH | N | CH | |
| A83 | CH | CH$_2$CN | Cl | CH | CH | N | |
| A84 | CH | CH$_2$CN | F | N | CH | CH | |
| A85 | CH | CH$_2$CN | F | CH | N | CH | |
| A86 | CH | CH$_2$CN | F | CH | CH | N | |
| A87 | N | CF$_3$ | H | N | CH | CH | |
| A88 | N | CF$_3$ | H | CH | N | CH | |
| A89 | N | CF$_3$ | H | CH | CH | N | |
| A90 | N | CF$_3$ | Cl | N | CH | CH | |
| A91 | N | CF$_3$ | Cl | CH | N | CH | |
| A92 | N | CF$_3$ | Cl | CH | CH | N | |
| A93 | N | CF$_3$ | F | N | CH | CH | |
| A94 | N | CF$_3$ | F | CH | N | CH | |
| A95 | N | CF$_3$ | F | CH | CH | N | |
| A96 | N | CH$_2$CN | H | N | CH | CH | |
| A97 | N | CH$_2$CN | H | CH | N | CH | |
| A98 | N | CH$_2$CN | H | CH | CH | N | |
| A99 | N | CH$_2$CN | Cl | N | CH | CH | |
| A100 | N | CH$_2$CN | Cl | CH | N | CH | |
| A101 | N | CH$_2$CN | Cl | CH | CH | N | |
| A102 | N | CH$_2$CN | F | N | CH | CH | |
| A103 | N | CH$_2$CN | F | CH | N | CH | |
| A104 | N | CH$_2$CN | F | CH | CH | N | |
| A105 | CH | CH$_2$CN | H | CH | CCl | CH | 175–176 |
| A106 | CH | CH$_2$CN | H | CH | CF | CH | 110–111 |
| A107 | CH | CF$_3$ | H | CH | CF | CH | 112–114 |
| A108 | CH | CF$_3$ | H | CH | CBr | CH | 87–88 |
| A109 | CH | CH$_2$CN | F | CH | CF | CH | 185–186 |
| A110 | N | CH$_2$CN | H | CH | CH | CH | 186–188 |
| A111 | CH | CF$_3$ | F | CH | CF | CH | 106–107 |
| A112 | CH | CH$_2$Cl | F | CH | CF | CH | 140–141 |
| A113 | CH | Me | F | CH | CF | CH | 173–174 |
| A114 | CH | CH$_2$CN | Cl | CH | CCl | CH | 211–214 |
| A115 | CH | CH$_2$CN | F | CH | CMe | CH | 178–181 |
| A116 | CH | CH$_2$Cl | Cl | CH | CH | CH | 142–143 |
| A117 | N | CH$_2$CN | Cl | CH | CCl | CH | yellow oil |
| A118 | CH | CH$_2$CN | F | CH | C(OMe) | CH | 161–163 |
| A119 | CH | CH$_2$CN | OMe | CH | CF | CH | 189–190 |
| A120 | CH | CH$_2$CN | F | CH | C(OEt) | CH | 115–116 |
| A121 | N | CH$_2$Cl | F | CH | CH | CH | 141–142 |
| A122 | CH | CH$_2$Cl | F | CH | CH | CH | 138–139 |
| A123 | CH | CH$_2$Br | F | CH | CH | CH | 137–138 |
| A124 | CH | CH$_2$CF$_3$ | F | CH | CH | CH | 141–142 |
| A125 | CH | CH$_2$CF$_3$ | Cl | CH | CH | CH | 153–154 |

EXAMPLES A126–A127

The following compounds of formula Ia where R$^2$ is H, R$^3$ and R$^4$ are both methoxy, A is =CR$^5$—, and Q is —CHMe—, may be prepared by methods as described hereinbefore:

| Ex | Y | R$^1$ | R$^5$ | B | D | E | M Pt (°C.) |
|---|---|---|---|---|---|---|---|
| A126 | CH | CH$_2$CN | H | CH | CH | CH | 133–135 |
| A127 | CH | CH$_2$CN | Cl | CH | CH | CH | 133–135 |

EXAMPLE B

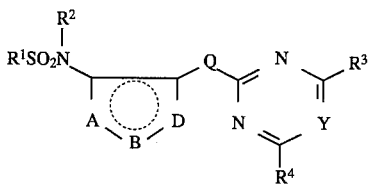

(Ib)

EXAMPLE B1

N-[3-(4,6-dimethoxypyrimidin-2-ylthio)-1,5-
dimethyl-1H-pyrazol-4
-yl]-1,1,1-trifluoromethanesulfonamide and
N-[5-(4,6-dimethoxypyrimidin-2-ylthio)-1,3-
dimethyl-1H-pyrazol-4
-yl]-1,1,1-trifluoromethanesulfonamide (a) 5-(4,6-Dimethoxypyrimidin-2-ylthio)-3-methyl
-4-nitro-1H-pyrazole 4,6-Dimethoxy-2-mercaptopyrimidine (4.65 g) was dissolved in water containing potassium hydroxide (1.7 g in 75 mls of water). 1,4-Dinitro-3-methylpyrazole (4.65 g) dissolved in the minimum of ethanol was then added dropwise. After the exothermic reaction had subsided, the mixture was stirred for 45 minutes. The precipitated solid was filtered off, washed with fresh water, and dried to give 6.3 g of the desired product, mp 175°–6° C.

(b) 5-(4,6-Dimethoxypyrimidin-2-ylthio)-1,3-
dimethyl-4-nitro-1H-pyrazole and
3-(4,6-Dimethoxypyrimidin-2-ylthio)-1,5-
dimethyl-4-nitro-1H-pyrazole The product of stage (a) above (3.15 g) was added in portions to a stirred slurry of 60% sodium hydride (0.47 g of 60%) in dry dimethylformamide (20 ml), with ice bath cooling. When the addition was complete, the reaction mixture was stirred for 10 minutes at room temperature. Iodomethane (1.7 g) was then added dropwise, and the mixture was stirred at room temperature for 2½, then poured into iced water (50 ml). It was then extracted with ethyl acetate (3×50 ml). The combined extracts were washed with water and dried over magnesium sulfate. Filtration, followed by evaporation, returned the crude product as an oil.

The crude product was subjected to flash chromatography on silica gel using a 1:1 mixture of ethyl acetate and 40°–60° petrol as eluent. Two new products were isolated. Evaporation of fractions containing pure products gave two different solid materials.

Thin layer chromatography on silica gel plates, using 1:1 ethyl acetate and 40–60 petrol eluent, gave one product with an Rf of about 0.75 (thought to be 5-(4,6-dimethoxypyrimidin-2 -ylthio)-1,3-dimethyl-4-nitro-1H-pyrazole), and the other with an Rf of about 0.3 (thought to be 3-(4,6-dimethoxypyrimidin-2-ylthio)-1,5-dimethyl-4-nitro-1H-pyrazole). Yield of product Rf 0.75=1.3 g, mp 124°–5° C. Yield of product Rf 0.3=0.82 g, mp 155°–6° C.

(c) 3-(4,6-Dimethoxypyrimidin-2-ylthio)-1,5-
dimethyl-1H-pyrazol-4-amine and
5-(4,6-Dimethoxypyrimidin-2-ylthio)-1,3-
dimethyl-1H-pyrazol-4-amine A mixture of the product of stage (b) (Rf 0.3) (2.4 g) and stannous chloride dihydrate (8.7 g) in ethanol (100 ml) was stirred at reflux for 4 hours. The ethanol was then removed in vacuo. The residue was stirred in water (100 ml) and basified with solid sodium hydrogen carbonate. Ethyl acetate (100 ml) was added and the emulsion filtered through a pad of kieselguhr. The organic layer was then separated. The solids were washed with fresh portions of ethyl acetate (75 ml in total) and the aqueous layer was extracted twice more with ethyl acetate (2×50 ml). The combined organic layers were washed with water (50 ml), then separated. After drying over magnesium sulfate, the ethyl acetate was evaporated to return an oil which crystallised. The crude product was purified by flash chromatography on silica gel using ethyl acetate as eluent. A new product Rf 0.3 (TLC on silica, ethyl acetate as eluent) was isolated. Evaporation of fractions containing pure new product gave 1.33 g of a solid mp 104°–5° C.

A similar procedure was employed to prepare the other isomer in a yield of 2.6 g, mp 74°–75° C.

(d) N-[3-(4,6-dimethoxypyrimidin-2-ylthio)-1,5-
dimethyl-1
H-pyrazol-4-yl]-1,1,1-trifluoromethanesulfonamide
(B1a) and
N-[5-(4,6-dimethoxypyrimidin-2-ylthio)-1,3-
dimethyl-1
H-pyrazol-4-yl]-1,1,1-trifluoromethanesulfonamide
(B1b)

Trifluoromethanesulfonic anhydride (1.2 g) in dry dichloromethane (10 mls) was added dropwise to a stirred solution of the aminopyrazole (Rf 0.3, 1.2 g), from stage (c) above, and pyridine (0.33 g) in dry dichloromethane (30 ml), at –60° C. (dry ice/acetone bath). When the addition was complete, the stirred mixture was allowed to come slowly to room temperature, and stirring was continued overnight. The dark red solution obtained was diluted to 100 ml with fresh dichloromethane, washed with water (25 ml), 1M Hcl (25 ml) and water (25 ml), and was then separated, and the organic layer dried over magnesium sulfate. Filtration, followed by evaporation, gave a dark red semi-solid. Flash chromatography using silica gel with 1:1 ethyl acetate/ 60–80 petrol as eluent gave a new product Rf 0.5 (TLC 1:1 ethyl acetate/60–80 petrol on silica gel plate). Evaporation of fractions containing pure new product gave the desired product (B1a) as a white solid in a yield of 0.83 g, mp 203°–4° C.

A similar procedure was employed to prepare the other isomer (B1b) in a yield of 1.8 g, mp 145°–6° C.

EXAMPLE B2

1-Cyano-N-[3-(4,6-dimethoxypyrimidin-2-ylthio)-1,5
-dimethyl-1H-pyrazol-4-yl]methanesulfonamide
(B2a) and
1-Cyano-N-[5-(4,6-dimethoxypyrimidin-2-ylthio)-1,3
-dimethyl-1H-pyrazol-4-yl]methanesulfonamide
(B2b)

The aminopyrazole from Example B1 stage (c) (Rf 0.3, 0.8 g) was dissolved in dry dichloromethane (10 ml) with stirring. Dry pyridine (0.23 g) was added. The mixture was cooled to –78° C. (dry ice/acetone bath), then cyanomethanesulfonyl chloride (0.4 g, 0.00285 mole) was added dropwise. The mixture was allowed to come slowly to room temperature, and was stirred for two days. It was then diluted to 100 ml with ethyl acetate and washed with water, 1M Hcl and water, separated, and the organic layer was dried over magnesium sulfate. Filtration and evaporation gave the crude product. Flash chromatography on silica gel using diethyl ether as eluent gave a new product Rf 0.4 (approx) [TLC on silica using diethyl ether as eluent]. Pure fractions were combined and evaporated to give the desired product (B2a) as a yellow solid (700 mg), mp 166°–7° C.

A similar procedure was employed to prepare the other isomer (B2b) as a solid in a yield of 1.6 g.

EXAMPLE B3

1-Cyano-N-[4-(4,6-dimethoxypyrimidin-2-ylthio)-1-methyl-1H-pyrazol-5-yl]methanesulfonamide (B3a) and
1-Cyano-N-[4-(4,6-dimethoxypyrimidin-2-ylthio)-1-methyl-1H-pyrazol-3-yl]methanesulfonamide (B3b)

(a) 2-(4,6-Dimethoxypyrimidin-2-ylthio)-3-(dimethylamino)acrylonitrile

A mixture of dimethylformamide dimethylacetal (5.8 g) and 2-(4,6-dimethoxypyrimidin-2-ylthio)acetonitrile (5.1 g) was stirred at 100° C. on an oil bath for 5 hrs. The reaction mixture was left to stand at room temperature overnight. Trituration of the crude solid with diisopropyl ether gave the desired product as a yellow solid in a yield of 5.4 g.

(b) 4-(4,6-Dimethoxypyrimidin-2-ylthio)-1-methylpyrazol-3-amine and
4-(4,6-Dimethoxypyrimidin-2-ylthio)-1-methylpyrazol-5-amine The product of stage (a) above (2.6 g) was stirred in glacial acetic acid (10 ml), and methyl hydrazine (1.0 g) was added dropwise. The mixture was then warmed to 100° C. on an oil bath for 3 hrs, allowed to cool, and poured into water (100 ml). The mixture was then neutralised with solid sodium hydrogen carbonate, and extracted with ethyl acetate (3×75 mls). The combined organic layers were washed with water (30 ml), then separated and dried over magnesium sulfate. Filtration followed by evaporation returned an oil. Flash column chromatography on silica gel using neat ethyl acetate as eluent gave essentially one component (Rf 0.3, TLC on silica using ethyl acetate as eluent). Pure fractions were combined and evaporated to return an off-white solid in a yield of 2.2 g. $^1$HNMR indicated a 50/50 mixture of the two possible isomeric products. The isomers obtained were then separated by preparative scale HPLC. Evaporation of the fractions containing the separate pure isomers gave both products as almost colourless crystals.

One product obtained was (A) in a yield of 480 mg, mp 110°–111° C. (thought to be 4-(4,6-Dimethoxypyrimidin-2-ylthio)-1-methylpyrazol-5-amine). The other product obtained was (B) (thought to be 4-(4,6-dimethoxypyrimidin-2-ylthio)-1-methylpyrazol-3-amine), in a yield of 800 mg, mp 160°–161° C.

(c) 1-Cyano-N-[4-(4,6-dimethoxypyrimidin-2-ylthio)-1-methyl-1H-pyrazol-5-yl]methanesulfonamide and
1-Cyano-N-[4-(4,6-dimethoxypyrimidin-2-ylthio)-1-methyl-1H-pyrazol-3-yl]methanesulfonamide The pyrazole (A) from stage (b) above (475 mg) was dissolved in dichloromethane (10 ml) with stirring. The mixture was then cooled to −78° C. (dry ice/acetone bath), and pyridine (0.15 ml) was added. Cyanomethanesulfonyl chloride (250 mg) in dichloromethane (1 ml) was added dropwise via a syringe. The mixture was then allowed to come slowly to room temperature, and was stirred overnight. After dilution to 100 ml with ethyl acetate, the mixture was washed with water (30 ml), dilute hydrochloric acid (2×30 ml) and saturated sodium chloride solution (30 ml). The organic layer was separated and dried over magnesium sulfate. Filtration, followed by evaporation, gave an off-white solid (thought to be 1-cyano-N-[4-(4,6-dimethoxypyrimidin-2-ylthio)-1-methyl-1H-pyrazol-5-yl]methanesulfonamide) (B3a) which was recrystallised from ethanol, yield 350 mg, mp 206°–7° C. The other isomer (B3b) was prepared by a similar method starting from pyrazole (B) from stage (b) above, yield 650 mg, mp 147°–8° C.

EXAMPLE B4

N-[3-(4,6-dimethoxy-1,3,5-triazin-2-ylmethyl)-1,5-dimethyl-1H-pyrazol-4-yl]-1,1,1-trifloromethanesulfonamide (a) Diethyl (5-methyl-4-nitropyrazol-3-yl)malonate Diethyl malonate (9.4 g) was added dropwise, with ice bath cooling, to a stirred slurry of sodium hydride (2.3 g of 60%) in dry tetrahydrofuran (100 ml). The mixture was then stirred for 10 minutes at ice-bath temperature, then 1,5-dinitro-3-methylpyrazole (5.0 g) was added in small portions over about 10 minutes, keeping the temperature at 10°–12° C., and the mixture was stirred for 30 minutes at room temperature. Glacial acetic acid (3 ml) was added continuously over about 5 minutes, and the mixture was diluted with ethyl acetate (400 ml), washed with water (2 portions of 30 ml). The organic layer was separated and dried over magnesium sulfate. Filtration, followed by evaporation, gave an oil which solidified on trituration with 60°–80° C. petrol to return 7.5 g of the desired product as a pale yellow solid, mp 100°–102° C.

(b) (5-Methyl-4-nitropyrazol-3-yl) acetic acid

A mixture of potassium hydroxide (5.9 g), the product of the above stage (7.5 g) and 50% aqueous ethanol (100 ml) was stirred at reflux for 1.5 hours, then allowed to cool, evaporated almost to dryness, diluted with water (100 ml) and acidified with concentrated hydrochloric acid. The resulting mixture was then heated to about 80° C. for ½ hour. After cooling, the mixture was evaporated to dryness. The residue was treated with ethyl acetate (100 ml) and washed with water (2 portions of 20 ml). The organic layer was separated and dried over magnesium sulfate. Filtration and evaporation gave 3.85 g of the the desired product as a yellow solid.

(c) Methyl (5-methyl-4-nitropyrazol-3-yl)acetate

The product of the above stage (3.85 g) was dissolved in methanol (75 ml) containing a few drops of concentrated sulphuric acid. The stirred mixture was boiled at reflux for 2 hours, and allowed to cool. The methanol was removed in vacuo and the residue dissolved in ethyl acetate and washed with water. The organic layer was separated and dried over magnesium sulphate. Filtration followed by evaporation and gave 4.0 g of the desired product as a cream coloured solid, mp 132°–3° C.

(d) Methyl (1,5-dimethyl-4-nitro-1H-pyrazol-3-yl)acetate and Methyl (1,3-dimethyl-4-nitro-1H-pyrazol-5-yl)acetate The product of the above stage (3.3 g) was added to a stirred mixture of potassium carbonate (2.5 g) and dimethyl formamide (30 ml). Iodomethane (2.6 g) was added in one portion producing a mildly exothermic reaction. The mixture was stirred at ambient temperature overnight, then diluted to 100 ml with water and extracted with diethyl ether (4 portions of 50 ml). The combined extracts were washed with water (30 ml) separated, dried over magnesium sulphate, filtered and evaporated to give 3.2 g of the desired mixed isomeric product as an oily solid.

(e) (1,5-Dimethyl-4-nitro-1H-pyrazol-3-yl) acetic acid and (1,3-Dimethyl-4-nitro-1H-pyrazol-5-yl) acetic acid The product of the above stage (3.2 g) was stirred in ethanol (25 ml). Potassium hydroxide (1.7 g) in water (25 ml) was added, and the mixture was stirred at reflux for 3 hours. It was then evaporated to near dryness and diluted to 50 ml with water. This solution was acidified with concentrated hydrochloric acid and evaporated, the residue being dissolved in ethyl acetate, washed with water and dried over magnesium sulfate. Filtration and evaporation gave 2.56 g of the desired mixed isomeric product as an orange solid.

(f) 2-(1,3-Dimethyl-4-nitro-1H-pyrazol-5-ylmethyl)-4,6-dimethoxy-1,3,5-triazine and 2-(1,5-Dimethyl-4-nitro-1H-pyrazol-3-ylmethyl)-4,6-dimethoxy-1,3,5-triazine The product from the above stage (2.56 g) was dissolved under nitrogen in dry dichloromethane (50 ml), and a nitrogen atmosphere was maintained for all subsequent procedures. Carbonyl diimidazole (2.0 g) was added and the mixture was stirred for 30 minutes, before being added dropwise to a stirred mixture of dimethyl imidodicarbonimidate zinc salt (2.1 g) and dichloromethane (50 ml) at −35° C. When complete, the mixture was allowed to warm to room temperature, and was stirred overnight. Water (50 ml) and dichloromethane (50 ml) were added and the mixture was filtered through Kieselguhr. It was then separated, and the aqueous layer was extracted further with dichloromethane (3 portions of 30 ml). The combined organic layers were washed with water and dried over magnesium sulfate. Evaporation gave 3.8 g of a crude product. Flash chromatography on silica gel using ethyl acetate as eluent gave two new products, Rf 0.6 and Rf about 0.4. The fractions containing the products were evaporated to give:

Rf 0.6: 1.0 g of 2-(1,3-dimethyl-4-nitro-1H-imidazol-5-yl)-4,6-dimethoxy-1,3,5-triazine, as a crystalline solid, and Rf 0.4: 1.0 g of 2-(1,5-dimethyl-4-nitro-1H-imidazol-3-yl)-4,6-dimethoxy-1,3,5-triazine, mp about 145° C.

(g) 2-(4-Amino-1,5-dimethyl-1H-imidazoll-3-ylmethyl)-4,6-dimethoxy-1,3,5-triazine 10% Palladium on charcoal (about 10 mg) was suspended in water (5 ml), and a solution of sodium borohydride (0.13 g) in water (5 ml) was added. Nitrogen was bubbled through the mixture, and the product of Rf 0.4 from the above stage (0.5 g) in methanol (30 ml) was added dropwise over 5 minutes. The mixture was left at room temperature for a further 30 minutes, after which acetic acid (1 ml) was added. The mixture was filtered through Kieselguhr, washing with fresh methanol, and was evaporated to near dryness, the residue being diluted to 15 ml with water, neutralised with solid sodium hydrogen carbonate, extracted with ethyl acetate (3 portions of 30 ml), and dried over magnesium sulfate. It was then filtered and evaporated to give 400 mg of the desired product as an orange viscous oil.

(h) N-[3-(4,6-dimethoxy-1,3,5-triazin-2-ylmethyl)-1,5-dimethyl-1H-pyrazol-4-yl]-1,1,1-trifluoromethanesulfonamide The product of the above stage (0.4 g) and pyridine (0.13 ml) were stirred and cooled to −60° C. in dichloromethane (15 ml). Trifluoromethanesulfonic anhydride (0.43 g) in dichloromethane (5 ml) was added slowly dropwise, and the mixture was allowed to come slowly to room temperature, at which it was stirred for 24 hours. It was then washed with water (10 ml), separated, and dried over magnesium sulfate. Filtration, followed by evaporation, gave 100 mg of the desired product as a pale yellow viscous oil.

EXAMPLE B5

1-Cyano-N-[5-(4,6-dimethoxypyrimidin-2-ylthio)-1,2-dimethyl-1H-imidazole-4-yl]methanesulfonamide

(a) 1,2-Dimethyl-4-bromo-5-nitro-1H-imidazole and 1,2-Dimethyl-5-bromo-4-nitro-1H-imidazole 2-Methyl-4-bromo-5-nitroimidazole (35 g) was dissolved in an aqueous solution of sodium hydroxide (7 g). Dimethyl sulfate (21.3 g) was added dropwise at room temperature and the reaction mixture was stirred for 2 hours. After the addition was complete, the resulting precipitate was filtered, washed with water and dried to give 33 g of a mixture of isomers which was separated by chromatography, eluting with petrol (60:80)/ethyl acetate (8:2) to give 9.4 g of 1,2-dimethyl-4-bromo-5-nitro-1H-imidazole, mp 98°–9° C., and 19.3 g of 1,2-dimethyl-5-bromo-4-nitro-1H-imidazole, mp 160°–162° C.

(b) 5-(4,6-Dimethoxypyrimidin-2-ylthio)-1,2-dimethyl-4-nitro-1H-imidazole 4,6-Dimethoxy-2-mercaptopyrimidine (3.0 g) was dissolved in an aqueous solution of sodium hydroxide (0.7 g in 100 ml water). 1,2-Dimethyl-5-bromo-4-nitro-1H-imidazole (3.9 g) dissolved in ethanol (50 ml) was added dropwise, and the mixture was stirred at room temperature for 6 hours. The precipitated product was filtered, washed with water, dried and recrystallised from acetonitrile to give 3.1 g of the desired product, mp 228°–30° C.

(C) 2,2,2-Trifluoro-N-[5-(4,6-dimethoxypyrimidin-2-ylthio)-1,2-dimethyl-1H-imidazole-4-yl]acetamide The product of the above stage (7.0 g), trifluoroacetic acid (130 ml), trifluoroacetic anhydride (18 ml) and iron powder (5.0 g) were heated with stirring to 70° C., and the mixture was maintained at that temperature for 8 hours. It was then filtered, and the filtrate poured into ice/water, basified with sodium hydroxide solution (5N), and extracted with ethyl acetate. The extracts were combined and dried over magnesium sulfate, and the solvent was removed. The residue was purified by chromatography eluting with petrol (60:80)/ethyl acetate 8:2, to give 5.0 g of the desired product, mp 160°-2° C.

(d) 5-(4,6-Dimethoxypyrimidin-2-ylthio)-1,2-dimethyl-1H-imidazol-4-amine

The product of the above stage (5.4 g) was dissolved in methanol (200 ml), potassium carbonate (1.5 g) was added, and the reaction mixture was heated to reflux for 6 hours. It was then filtered, the solvent was removed, and the residue was recrystallised from acetonitrile, to give 2.6 g of the desired product.

(e) 1-Cyano-N-[5-(4,6-dimethoxypyrimidin-2-ylthio)-1,2-dimethyl-1H-imidazole-4-yl]methanesulfonamide The product of the above stage (1.0 g) was dissolved in dichloromethane (10 ml), pyridine (0.3 g) was added, and the reaction mixture was cooled to –45° C. Cyanomethylsulfonyl chloride (0.5 g) was added in one portion, and the mixture was stirred for a further 30 minutes at –45° C. It was then allowed to warm to room temperature, and was stirred overnight at room temperature. It was then poured into water, extracted with ethyl acetate, and purified by chromatography, eluting with petrol 60:80)/ethyl acetate (8:2) to give 0.7 g of the desired product, mp 223°-225° C.

EXAMPLE B6

1-Cyano-N-[2-(4,6-dimethoxypyridin-2-ylthio)-3-thienyl]methanesulfonamide (a) 4,6-Dimethoxy-2-(3-nitro-2-thienylthio) pyrimidine Sodium hydroxide (1.2 g) was dissolved in water (50 ml), 4,6-dimethoxy-2-mercaptopyrimidine (5.3 g) was added, and the mixture was stirred at room temperature for 15 minutes. 2-Chloro-3-nitrothiophene (5.0 g) dissolved in ethanol (50 ml) was added with stirring, the mixture being stirred at room temperature for 6 hours. The resulting precipitate was filtered, washed with water and dried, to give 7.6 g of the desired product, mp 199°-201° C.

(b) N-[2-(4,6-dimethoxypyrimidin-2-ylthio)-3-thienyl]-2,2,2-trifluoroacetamide

The product of the above stage (2.0 g) was dissolved in trifluoroacetic acid (50 ml), and trifluoroacetic anhydride (5.0 ml) and iron powder (1.8 g) were added. The reaction mixture was stirred with heating to 70° C. and was maintained at that temperature for 8 hours, after which it was filtered, and the filtrate was poured into ice/water, basified with sodium hydroxide solution (5N), extracted with ethyl acetate, dried over magnesium sulfate, and evaporated to low bulk. The product crystallised to give 1.2 g of the desired product, mp 88°-90° C.

(c) 2-(4,6-Dimethoxypyrimidin-2-ylthio) thiophene-3-amine

The product of the above stage (2.2 g) was dissolved in methanol (30 ml), potassium carbonate (1.0 g) was added, and the reaction mixture was heated with stirring to 40° C., at which it was maintained for 8 hours. It was then allowed to cool, and was filtered. The filtrate was evaporated, the residue being purified by flash chromatography eluting with petrol (60:80)/ethyl acetate (8:2) to give 1.0 g of the desired product as an orange oil.

(d) 1-Cyano-N-(2-(4,6-dimethoxypyridin-2-ylthio)-3-thienyl]methanesulfonamide

The product of the above stage (1.2 g) and pyridine (1.0 ml) were dissolved in dichloromethane (10 ml), and the mixture was cooled to –78° C. with stirring. A solution of cyanomethanesulfonyl chloride (0.6 g) in dichloromethane (5 ml) was added dropwise, keeping the temperature at –78° to –60° C., and the mixture was stirred for 15 minutes at –78° C. After the addition was complete, the mixture was allowed to warm to room temperature, stirred for further 16 hours, poured into water and extracted with dichloromethane. The extracts were combined and dried over magnesium sulfate, and the solvent was removed. The residue was purified by chromatography eluting with petrol (60:80)/ethyl acetate (8:2) to give 0.4 g of the desired product, mp 118°-120° C.

EXAMPLE B7

N-[2-(4,6-dimethoxypyrimidin-2-ylthio)-3-thienyl]-1,1,1-trifluoromethanesulfonamide The product of Example B6 stage (c) (1.0 g) and pyridine (0.6 g) were dissolved in dichloromethane (25 ml), and the mixture was cooled to –78° C. A solution of trifluoromethane sulfonic anhydride (1.1 g) in dichloromethane (5 ml) was added dropwise to the reaction mixture, maintaining the temperature at –78° to –60° C. After the addition was complete, the reaction mixture was stirred for 15 minutes at –78° C. before being allowed to warm to room temperature. It was then stirred overnight at room temperature, poured into water, and extracted with dichloromethane. The extracts were combined, and were dried over magnesium sulfate. The solvent was removed, and the residue was purified by chromatography eluting with petrol (60:80)/ethyl acetate (8:2), to give the desired product (B7a), mp 103°-104° C., and also the corresponding compound where $R^2$ is —$SO_2CF_3$ (B7b), mp 136°-138° C.

EXAMPLE B8

The following compounds of formula Ib where $R^2$ is hydrogen, $R^3$ and $R^4$ are both methoxy, and Q is —$CH_2$—, may be prepared by methods as described hereinbefore:

| Y | A | B | D | $R^1$ |
|---|---|---|---|---|
| CH | S | CH | CH | $CF_3$ |
| CH | N(Me) | CH | CH | $CF_3$ |
| CH | S | CH | N | $CF_3$ |
| CH | S | N | CH | $CF_3$ |
| CH | N(Me) | CH | N | $CF_3$ |
| CH | N(Me) | N | CH | $CF_3$ |
| CH | CH | S | CH | $CF_3$ |
| CH | CH | N(Me) | CH | $CF_3$ |
| CH | CH | N(Me) | CH | $CF_3$ |
| CH | CH | S | N | $CF_3$ |
| CH | N | S | CH | $CF_3$ |
| CH | N | N(Me) | CH | $CF_3$ |
| CH | CCl | S | CH | $CF_3$ |
| CH | CCl | N(Me) | N | $CF_3$ |
| CH | CCl | S | N | $CF_3$ |
| CH | CCl | N(Me) | N | $CF_3$ |
| CH | CF | S | CH | $CF_3$ |
| CH | CF | N(Me) | N | $CF_3$ |
| CH | CF | S | N | $CF_3$ |

-continued

| Y | A | B | D | R¹ |
|---|---|---|---|---|
| CH | CF | N(Me) | N | CF₃ |
| CH | CH | CH | S | CF₃ |
| CH | CH | CH | N(Me) | CF₃ |
| CH | N | CH | S | CF₃ |
| CH | CH | N | S | CF₃ |
| CH | CH | N | N(Me) | CF₃ |
| CH | N | CH | N(Me) | CF₃ |
| CH | CCl | CH | S | CF₃ |
| CH | CCl | CH | N(Me) | CF₃ |
| CH | CCl | N | S | CF₃ |
| CH | CCl | N | N(Me) | CF₃ |
| CH | CF | CH | S | CF₃ |
| CH | CF | CH | N(Me) | CF₃ |
| CH | CF | N | S | CF₃ |
| CH | CF | N | N(Me) | CF₃ |
| N | S | CH | CH | CF₃ |
| N | N(Me) | CH | CH | CF₃ |
| N | S | CH | N | CF₃ |
| N | S | N | CH | CF₃ |
| N | N(Me) | CH | N | CF₃ |
| N | N(Me) | N | CH | CF₃ |
| N | CH | S | CH | CF₃ |
| N | CH | N(Me) | CH | CF₃ |
| N | CH | N(Me) | CH | CF₃ |
| N | N | S | N | CF₃ |
| N | N | N(Me) | CH | CF₃ |
| N | CCl | S | CH | CF₃ |
| N | CCl | N(Me) | N | CF₃ |
| N | CCl | S | N | CF₃ |
| N | CCl | N(Me) | N | CF₃ |
| N | Cp | S | CH | CF₃ |
| N | CF | N(Me) | N | CF₃ |
| N | CF | S | N | CF₃ |
| N | CF | N(Me) | N | CF₃ |
| N | CH | CH | S | CF₃ |
| N | CH | CH | N(Me) | CF₃ |
| N | N | CH | N(Me) | CF₃ |
| N | CH | N | S | CF₃ |
| N | CH | N | N(Me) | CF₃ |
| N | N | CH | N(Me) | CF₃ |
| N | CCl | CH | S | CF₃ |
| N | CCl | CH | N(Me) | CF₃ |
| N | CCl | N | S | CF₃ |
| N | CCl | N | N(Me) | CF₃ |
| N | CF | CH | S | CF₃ |
| N | CF | CH | N(Me) | CF₃ |
| N | CF | N | S | CF₃ |
| N | CF | N | N(Me) | CF₃ |
| CH | S | CH | CH | CH₂CN |
| CH | N(Me) | CH | CH | CH₂CN |
| CH | S | CH | N | CH₂CN |
| CH | S | N | CH | CH₂CN |
| CH | N(Me) | CH | N | CH₂CN |
| CH | N(Me) | N | CH | CH₂CN |
| CH | CH | S | CH | CH₂CN |
| CH | CH | N(Me) | CH | CH₂CN |
| CH | CH | N(Me) | CH | CH₂CN |
| CH | CH | S | N | CH₂CN |
| CH | N | S | CH | CH₂CN |
| CH | N | N(Me) | CH | CH₂CN |
| CH | CCl | S | CH | CH₂CN |
| CH | CCl | N(Me) | N | CH₂CN |
| CH | CCl | S | N | CH₂CN |
| CH | CCl | N(Me) | N | CH₂CN |
| CH | CF | S | CH | CH₂CN |
| CH | CF | N(Me) | N | CH₂CN |
| CH | CF | S | N | CH₂CN |
| CH | CF | N(Me) | N | CH₂CN |
| CH | CH | CH | N(Me) | CH₂CN |
| CH | N | CH | S | CH₂CN |
| CH | CH | N | S | CH₂CN |
| CH | CH | N | N(Me) | CH₂CN |
| CH | N | CH | N(Me) | CH₂CN |
| CH | CCl | CH | S | CH₂CN |
| CH | CCl | CH | N(Me) | CH₂CN |
| CH | CCl | N | S | CH₂CN |
| CH | CCl | N | N(Me) | CH₂CN |
| CH | CF | CH | S | CH₂CN |
| CH | CF | CH | N(Me) | CH₂CN |
| CH | CF | N | S | CH₂CN |
| CH | CF | N | N(Me) | CH₂CN |
| N | S | CH | CH | CH₂CN |
| N | N(Me) | CH | CH | CH₂CN |
| N | S | CH | N | CH₂CN |
| N | S | N | CH | CH₂CN |
| N | N(Me) | CH | N | CH₂CN |
| N | N(Me) | N | CH | CH₂CN |
| N | CH | S | CH | CH₂CN |
| N | CH | N(Me) | CH | CH₂CN |
| N | CH | N(Me) | CH | CH₂CN |
| N | CH | S | N | CH₂CN |
| N | N | S | CH | CH₂CN |
| N | N | N(Me) | CH | CH₂CN |
| N | CCl | S | CH | CH₂CN |
| N | CCl | N(Me) | N | CH₂CN |
| N | CCl | S | N | CH₂CN |
| N | CCl | N(Me) | N | CH₂CN |
| N | CF | S | CH | CH₂CN |
| N | CF | N(Me) | N | CH₂CN |
| N | CF | S | N | CH₂CN |
| N | CF | N(Me) | N | CH₂CN |
| N | CH | CH | S | CH₂CN |
| N | CH | CH | N(Me) | CH₂CN |
| N | N | CH | S | CH₂CN |
| N | CH | N | S | CH₂CN |
| N | CH | N | N(Me) | CH₂CN |
| N | N | CH | N(Me) | CH₂CN |
| N | CCl | CH | S | CH₂CN |
| N | CCl | CH | N(Me) | CH₂CN |
| N | CCl | N | S | CH₂CN |
| N | CCl | N | N(Me) | CH₂CN |
| N | CF | CH | S | CH₂CN |
| N | CF | CH | N(Me) | CH₂CN |
| N | CF | N | S | CH₂CN |
| N | CF | N | N(Me) | CH₂CN |

EXAMPLE C

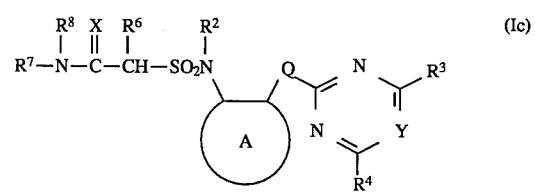

(Ic)

EXAMPLE C1

2-[2-(4,6-Dimethoxypyrimidin-2-yloxy)-6-fluorophenylsulfamoyl]-N-methylacetamide (a) Methyl [2-(4,6-dimethoxypyrimidin-2-yloxy)-6-fluorophenylsulfamoyl]acetate Methyl (chlorosulfonyl)acetate (13.0 g) in dichloromethane (20 ml) was added dropwise with stirring and cooling to 2-(4,6-dimethoxypyrimidin-2-yloxy)-6-fluoroaniline (20 g) and pyridine (6.3 g) in dichloromethane (120 ml). After stirring for 2 hours, the mixture was allowed to stand at room temperature overnight. Washing with dilute hydrochloric acid and water, drying over magnesium sulfate, and running down, gave an oil which was triturated with ether. The resulting off-white solid was separated by filtration to give 20.4 g of the desired product, mp 111°–114° C.

(b) 2-[2-(4,6-Dimethoxypyrimidin-2-yloxy)-6-fluorophenylsulfamoyl]-N-methylacetamide Methylamine (4.2 g of a 33% solution in industrial methylated spirits) was added to a solution of the product of stage (a) (3 g) in methanol (60 ml) at room temperature. After standing for 23 days, the solution was run down under vacuum at less than 35° C. to give a brown oil. Trituration with a mixture of diethyl ether and isopropanol gave an off-white solid which was dried without heat to give 1.3 g of the desired product, mp 193°–198° C.

EXAMPLE C2

2-[2-(4,6-Dimethoxypyrimidin-2-yloxy)-6-fluorophenylsulfamoyl]thioacetamide Hydrogen sulfide gas was bubbled into a solution of [2-(4,6-dimethoxypyrimidin-2-yloxy)-6-fluorophenylsulfamoyl]acetonitrile (8.0 g) in pyridine (40 ml) and triethylamine (2.2 g) at 0°–5° C. over 3 hours. The solution was allowed to warm to room temperature with continued addition of hydrogen sulfide for a further 3 hours. After standing overnight, the reaction mixture was made up to 500 ml with ice/water, was acidified with hydrochloric acid and extracted with dichloromethane three times. The organic phase was washed with water twice, and was dried over magnesium sulfate. The dichloromethane was removed under vacuum at less than 35° C. The resulting residue was washed with ether to give an off-white solid which was dried without heat to give 4.8 g of the desired compound, mp 156°–158° C.

EXAMPLES C3–C6

The following compounds of formula Ic in which A is a benzene ring substituted in the ortho position relative to the sulfonamido group as set out below, X and Q are both oxygen, $R^3$ and $R^4$ are both methoxy, Y is —CH=, and $R^2$, $R^6$ and $R^8$ are all hydrogen, were prepared by methods analogous to that of Example C1:

| Ex | Subst | R | M Pt (°C.) |
| --- | --- | --- | --- |
| C3 | Cl | H | 156–157 |
| C4 | Cl | Me | 202–204 |
| C5 | F | H | 136–140 |
| C6 | F | n-Pr | 120–124 |

HERBICIDAL EXAMPLE A (Pre-Emergence)

Seeds of the test species listed below were each sown in 8.5 cm square pots filled to within 2 cm of the top with sterile loam, and were covered with a 2–5 mm layer of loam. The pots were watered, and then treated by application to the soil surface in a spray cabinet with the compounds of the Examples listed below formulated as a solution/suspension in 3:1 by volume of acetone and the wetting agent polyoxyethylene (20 mols) monolaurate solution (10 g per liter). The concentration of each test compound and volume of application were calculated to give the desired rate of application of the compound in 200 liters per hectare.

After 3 to 4 weeks growth in a glasshouse (minimum temperature 16° C. for temperate species, 21° C. for non-temperate species, 16 hours per day photoperiod), the plants were visually assessed for any herbicidal response. All differences from an untreated control were scored accordingly to an index where 0=no effect, 1=1–24% effect, 2=25–69% effect, 3=70–89% effect and 4=90–100% effect. In the table below, the following letters are used to denote the plant species:

a—*Triticum aestivum* (wheat)
b—*Hordeum vulgare* (barley)
c—*Beta vulgaris* (sugar beet)
d—*Brassica napus* (rape)
e—*Alopecurus myosuroides* (blackgrass)
f—*Avena fatua* (wild oat)
g—*Elymus repens* (couch)
h—*Bromus sterilis* (barren brome)
i—*Viola arvensis* (field pansy)
j—*Stellaria media* (chickweed)
k—*Galium aparine* (cleavers)
l—*Matricaria inodora* (scentless mayweed)
m—*Polygonum lapathifolium* (Pale persicaria)
n—*Veronica persicae* (Buxbaum's speedwell).

The results obtained were as follows:

| Ex | Kg/ha | a | b | c | d | e | f | g | h | i | j | k | l | m | n |
| --- | --- | --- | --- | --- | --- | --- | --- | --- | --- | --- | --- | --- | --- | --- | --- |
| A1 | 0.25 | 1 | 1 | 3 | 4 | 2 | 1 | 3 | 1 | 2 | 4 | 3 | 4 | 3 | 4 |
| A3 | 0.5 | 0 | 0 | 2 | 4 | 0 | 0 | 0 | 0 | 2 | 2 | 3 | 4 | 2 | 3 |
| A6 | 0.25 | 1 | 0 | 3 | 4 | 1 | 0 | 0 | 2 | 4 | 4 | 4 | 4 | 3 | 4 |
| A7 | 0.25 | 1 | 0 | 3 | 2 | 1 | 1 | 0 | 0 | 3 | 4 | 3 | 4 | 2 | 4 |
| A8 | 0.125 | 2 | 2 | 3 | 4 | 2 | 1 | 2 | 2 | 3 | 4 | 3 | 4 | 2 | 4 |
| A9 | 0.125 | 0 | 1 | 2 | 2 | 2 | 0 | 0 | 2 | 3 | 4 | 3 | 4 | 2 | 4 |
| A16 | 0.125 | 2 | 1 | 4 | 4 | 2 | 2 | 2 | 1 | 3 | 4 | 4 | 4 | 3 | 4 |
| A17 | 0.063 | 0 | 0 | 1 | 3 | 0 | 0 | 0 | 0 | 2 | 3 | 2 | 3 | 2 | 2 |
| A108 | 0.5 | 0 | 0 | 2 | 2 | 0 | 0 | 0 | 0 | 2 | 2 | 2 | 4 | 0 | 2 |
| A109 | 0.5 | 0 | 0 | 3 | 3 | 0 | 0 | 1 | 0 | 4 | 3 | 3 | 4 | 2 | 4 |
| A111 | 0.125 | 0 | 1 | 1 | 1 | 0 | 0 | 0 | 0 | 1 | 1 | 2 | 3 | 0 | 3 |
| A112 | 0.125 | 0 | 1 | 2 | 1 | 0 | 0 | 0 | 1 | 3 | 4 | 3 | 4 | 1 | 3 |
| A114 | 0.5 | 0 | 0 | 2 | 2 | 0 | 0 | 0 | 0 | 2 | 3 | 1 | 3 | 1 | 3 |
| A115 | 0.5 | 0 | 0 | 2 | 2 | 0 | 0 | 0 | 2 | 3 | 4 | 3 | 4 | 3 | 4 |
| A116 | 0.25 | 1 | 1 | 2 | 4 | 1 | 0 | 0 | 1 | 3 | 4 | 4 | 4 | 2 | 4 |
| B1 | 0.5 | 0 | 1 | 2 | 3 | 1 | 0 | 2 | 1 | 2 | 2 | 3 | 4 | 2 | 3 |

HERBICIDAL EXAMPLE B (Post-Emergence)

The plant species listed below were grown in 8.5 cm square pots containing sterile loam in a glasshouse (minimum temperature 16° C. for temperate species, 21° C. for non-temperate species, 16 hours per day photoperiod), and were treated in a spray cabinet at the 2–3 leaf stage with the compounds of the Examples listed below formulated as a solution/suspension in 3:1 by volume of acetone and the wetting agent polyoxyethylene (20 mols) monolaurate solution (10 g per liter). The concentration of each test compound and volume of application were calculated to give the desired rate of application of the compound in 200 liters per hectare.

After 3-4 weeks, the plants were visually assessed for any herbicidal response. All differences from an untreated control were scored according to an index where 0=no effect, 1=1-24% effect, 2=25-69% effect, 3=70-89% effect and 4=90-100% effect.

In the table below, the letters used denote the same plant species as in Herbicidal Example A:

The results obtained were as follows:

| Ex | Kg/ha | a | b | c | d | e | f | g | h | i | j | k | l | m | n |
|---|---|---|---|---|---|---|---|---|---|---|---|---|---|---|---|
| A1 | 0.5 | 0 | 0 | 2 | 4 | 0 | 0 | 0 | 0 | 0 | 2 | 4 | 4 | 2 | 2 |
| A3 | 0.5 | 0 | 0 | 1 | 4 | 1 | 0 | 0 | 0 | 1 | 2 | 4 | 4 | 1 | 2 |
| A5 | 0.5 | 1 | 1 | 1 | 3 | 1 | 0 | 1 | 1 | 2 | 1 | 2 | 2 | 1 | 2 |
| A6 | 0.25 | 1 | 0 | 4 | 4 | 2 | 2 | 2 | 2 | 3 | 3 | 4 | 4 | 3 | 2 |
| A7 | 0.25 | 1 | 1 | 2 | 4 | 2 | 2 | 2 | 2 | 3 | 3 | 4 | 2 | 2 | 3 |
| A8 | 0.25 | 1 | 0 | 4 | 4 | 2 | 0 | 2 | 0 | 4 | 4 | 4 | 4 | 2 | 2 |
| A9 | 0.125 | 1 | 1 | 3 | 4 | 0 | 0 | 1 | 0 | 3 | 3 | 4 | 4 | 2 | 2 |
| A16 | 0.032 | 1 | 1 | 3 | 4 | 1 | 0 | 0 | 0 | 2 | 4 | 4 | 3 | 3 | 1 |
| A17 | 0.25 | 0 | 0 | 4 | 4 | 0 | 0 | 0 | 0 | 2 | 4 | 4 | 4 | 3 | 1 |
| A109 | 0.5 | 1 | 0 | 4 | 4 | 1 | 0 | 1 | 0 | 2 | 3 | 4 | 4 | 2 | 3 |
| A111 | 0.25 | 0 | 0 | 2 | 3 | 1 | 0 | 0 | 0 | 0 | 0 | 3 | 3 | 0 | 2 |
| A112 | 0.25 | 0 | 0 | 2 | 3 | 0 | 0 | 0 | 0 | 0 | 2 | 4 | 0 |   | 2 |
| A114 | 0.25 | 0 | 0 | 0 | 2 | 0 | 0 | 0 | 0 | 0 | 0 | 2 | 0 | 0 | 0 |
| A115 | 0.25 | 0 | 0 | 1 | 4 | 0 | 0 | 0 | 0 | 0 | 2 | 3 | 2 | 3 | 0 |
| A116 | 0.25 | 0 | 0 | 4 | 4 | 1 | 0 | 0 | 0 | 2 | 4 | 4 | 2 | 2 | 2 |
| A117 | 0.125 | 0 | 0 | 3 | 4 | 0 | 0 | 0 | 0 | 0 | 3 | 4 | 2 | 2 | 2 |
| A118 | 0.125 | 0 | 0 | 1 | 0 | 0 | 0 | 0 | 0 | 0 | 3 | 0 | 3 | 0 |   |
| A119 | 0.063 | 1 | 0 | 1 | 1 | 0 | 0 | 0 | 0 | 0 | 2 | 0 | 1 | 1 |   |
| B1 | 0.5 | 0 | 1 | 2 | 4 | 2 | 0 | 1 | 0 | 0 | 3 | 3 | 4 | 1 | 2 |

We claim:

1. A sulfonamide of the formula:

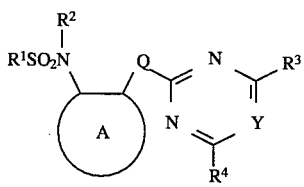

I or a salt thereof, where:

A represents a substituted or unsubstituted benzene, or a 5-membered unsubstituted or substituted heteroaromatic ring selected from the group consisting of unsubstituted or substituted thiophene, furan, pyrrole, thiazole, isothiazole, pyrazole, imidazole, oxazole and isoxazole ring, any substituent on a carbon atom of which is halo, cyano, a group $-COOR^{10}$ where $R^{10}$ represents hydrogen or an optionally-substituted alkyl group, or an optionally-substituted alkyl, alkoxy, aryloxy, heterocyclyloxy or amino group, and any substituent on a nitrogen atom of the ring A is a substituted or unsubstituted alkyl, alkoxy, amino or aryl group;

Q is $-O-$, $-S-$ or a group $-CXX'-$;

X and X', which may be the same or different, are each hydrogen, halogen, cyano, an optionally-substituted alkyl group or a group $-OR^a$, $-SR^a$, or $-COR^b$; or one of X and X' represents hydroxy and the other is as defined above; or X and X' together represent $=O$ or $=S$;

$R^a$ is an optionally-substituted alkyl, aryl or acyl group;

$R^b$ is an optionally-substituted alkyl or aryl group, or a group $-OR^c$ or $-NR^cR^d$;

$R^c$ and $R^d$, which may be the same or different, are each hydrogen, or an optionally-substituted alkyl or aryl group;

Y is a group $CR^9$;

$R^1$ is an optionally-substituted alkyl, alkenyl, alkynyl, cycloalkyl, aryl, heterocyclyl, benzoheterocyclyl or amino group;

$R^2$ is hydrogen, an optionally-substituted alkyl or carboxylic acyl group, or a group $-SO_2R^1$;

$R^3$ and $R^4$, which may be the same or different, are each hydrogen, halo, an optionally-substituted alkyl, alkoxy, cycloalkyl or amino group, or an optionally substituted heterocyclyl group; and $R^9$ represents hydrogen or an optionally-substituted alkyl group;

with the proviso that when Q is $-O-$ or $-S$, the ring A is a substituted or unsubstituted heteroaromatic group, and with the proviso that when $R^1$ is substituted alkyl, it is not:

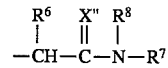

in which X" is oxygen or sulfur, and $R^6$, $R^7$ and $R^8$, which may be the same or different, are each hydrogen or an optionally-substituted alkyl group;

provided always that:

any alkyl group in the molecule is of 1 to 8 carbon atoms and, when substituted, is so by one or more halogen atoms, alkoxy or alkylthio groups of 1 to 4 carbon atoms, hydroxy, nitro, mercapto, amino, substituted amino, carbamoyl, substituted carbamoyl, thiocarbamoyl, substituted thiocarbamoyl, cyano, acyl, aryl or heteroaryl groups;

any alkenyl or alkynyl group in the molecule is of 2 to 6 carbon atoms which, when substituted, is so by halogen;

any cycloalkyl group in the molecule is of 3 to 7 carbon atoms;

any aryl group in the molecule is a phenyl group which, when substituted, is so by one or more alkyl, alkoxy, alkoxycarbonyl or alkylthio groups of 1 to 4 carbon atoms (which may themselves be further substituted), halogen atoms, cyano groups, aminosulfonyl groups or nitro groups;

any heterocyclyl group in the molecule, other than the ring A, is furyl, thienyl, pyrrolyl, oxazolyl, isoxazolyl, isothiazolyl, pyrimidinyl, triazolyl or imidazolyl or, for $R^1$ only, may be pyridyl, thiazolotriazolyl, triazolopyrimidinyl or pyrazolopyrimidinyl;

any benzoheterocyclyl group in the molecule is a benzothiophene, benzodioxole, quinoline, quinazoline, benzothiazole or dihydrobenzofuran group;

any substituted amino group in the molecule is mono- or di-substituted by alkyl of 1 to 4 carbon atoms, alkenyl of 2 to 4 carbon atoms, carbamoyl, carboxylic acyl, alkoxycarbonyl, alkylcarbamoyl or dialkylcarbamoyl in which any alkyl group is of 1 to 4 carbon atoms; and the term 'acyl' means alkanoyl, alkenoyl, alkynoyl, cycloalkanoyl, aralkanoyl, aroyl, carbamoyl, thiocarbamoyl, alkoxycarbonyl, sulfonyl, sulfamoyl or phosphonyl groups, in which any alkyl, alkenyl, alkynyl or aryl group may be substituted or unsubstituted.

2. The sulfonamide according to claim 1 in which $R^1$ is methyl, chloromethyl, bromomethyl, cyanomethyl, trifluoromethyl, methoxycarbonylmethyl, 2-chlorophenyl, methoxycarbonylamino or thiazolotriazolyl.

3. The sulfonamide according to claim 1 in which $R^2$ is hydrogen.

4. The sulfonamide according to claim 1, in which $R^3$ and $R^4$ are each hydrogen, methyl, methoxy or chloro.

5. The sulfonamide according to claim 1 in which the ring A is phenyl (optionally substituted by fluorine, chlorine, bromine, methyl, methoxy or ethoxy), or pyrazolyl (optionally substituted by one or more methyl groups).

6. The sulfonamide according to claim 1 in which Q is —CH$_2$—, —CH(CH$_3$)—, —S— or —O—.

7. The sulfonamide according to claim 1, in which $R^2$ and $R^9$ are hydrogen, $R^3$ and $R^4$ are methoxy, Q is CH$_2$ or S.

8. The sulfonamide according to claim 7, in which Q is CH$_2$, $R^1$ is CF$_3$, CH$_2$CN or CH$_2$Cl and A is a benzene ring which is unsubstituted or is substituted with fluorine, chlorine, bromine, methyl or methoxy.

9. A herbicidal composition which comprises a compound according to claim 8, in association with at least one carrier or surface active agent.

10. A method of combating weeds at a locus infested or liable to be infested therewith, which comprises applying to said locus an effective amount of a compound according to claim 8.

11. The sulfonamide according to claim 8, in which the phenyl ring is either unsubstituted or substituted with fluorine or chlorine and in which $R^1$ is CF$_3$ or CH$_2$CN.

12. The sulfonamide according to claim 7, in which Q is sulfur and A is a 5 membered substituted heteroaromatic ring substituted by alkyl and $R^1$ is halogen substituted alkyl.

13. A herbicidal composition which comprises a compound according to claim 12, in association with at least one carrier or surface active agent.

14. A method of combating weeds at a locus infested or liable to be infested therewith, which comprises applying to said locus an effective amount of a compound according to claim 12.

15. A herbicidal composition which comprises a compound according to claim 1, in association with at least one carrier or surface active agent.

16. A method of combating weeds at a locus infested or liable to be infested therewith, which comprises applying to said locus an effective amount of a compound according to claim 1.

17. A process for the preparation of a sulfonamide according to claim 1 in which an amine of the formula:

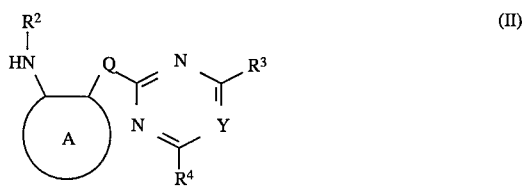

(II)

where A, Q, Y, and $R^2$ to $R^4$ are as defined in claim 1 is reacted with a suitable sulfonic anhydride of the formula $(R^1SO_2)_2O$ or sulfonyl halide of the formula $R^1SO_2Hal$, where Hal is a halogen atom and $R^1$ is as defined in claim 1, to give the desired compound.

* * * * *